United States Patent [19]

Mitchen

[11] Patent Number: 4,844,098
[45] Date of Patent: Jul. 4, 1989

[54] NON-INVASIVE COLLECTION MEANS AND METHOD

[76] Inventor: Joel R. Mitchen, 7418 - 41st Ave., Kenosha, Wis. 53142

[21] Appl. No.: 112,864

[22] Filed: Oct. 23, 1987

Related U.S. Application Data

[63] Continuation-in-part of Ser. No. 574,901, Jan. 30, 1984, abandoned, and a continuation-in-part of Ser. No. 759,618, Jul. 26, 1985, abandoned.

[51] Int. Cl.⁴ ............................................. A61B 5/00
[52] U.S. Cl. ................................... 128/765; 604/316; 604/290
[58] Field of Search ............................... 128/765–767; 604/19, 22, 116, 289, 290, 310, 312, 313, 315, 316

[56] References Cited

U.S. PATENT DOCUMENTS

| | | | |
|---|---|---|---|
| 680,723 | 8/1901 | Maurer | 604/289 |
| 1,212,945 | 1/1917 | Haslam . | |
| 2,194,173 | 3/1940 | Van Tyen | 604/313 |
| 2,249,500 | 7/1941 | Shirley et al. | 604/315 |
| 2,594,959 | 4/1952 | Masters | 604/310 |
| 3,315,665 | 4/1967 | MacLeod | 604/315 |
| 3,520,292 | 11/1966 | Barr et al. | 604/413 |
| 3,763,854 | 10/1973 | Welch | 604/315 |
| 3,782,387 | 1/1974 | Falabella | 604/315 |
| 3,794,035 | 2/1974 | Brenner | 604/315 |
| 3,810,458 | 5/1974 | Semp | 128/1 R |
| 3,815,579 | 6/1974 | Rose | 128/2 F |
| 3,906,940 | 9/1975 | Kawada | 604/315 |
| 4,151,832 | 5/1979 | Hamer | 128/765 |
| 4,248,230 | 2/1981 | Marinello | 128/268 |
| 4,250,878 | 2/1981 | Jacobsen et al. | 128/207.21 |
| 4,291,015 | 9/1981 | Keith et al. | 424/28 |
| 4,396,023 | 8/1983 | Anderson | 128/760 |
| 4,542,750 | 9/1985 | Ettare | 604/312 |

FOREIGN PATENT DOCUMENTS

| | | | |
|---|---|---|---|
| 2241285 | 3/1975 | France | 604/312 |
| 7507925 | 10/1976 | France | 604/313 |
| 2126900 | 4/1984 | United Kingdom | 604/313 |

*Primary Examiner*—Max Hindenburg
*Attorney, Agent, or Firm*—Quarles & Brady

[57] ABSTRACT

A non-invasive method for collecting tissue fluids from a human or an animal which comprises pretreating the external surface of an area of the skin of the human or the animal with a solution to clean off dead cells, forming a liquid coating over the skin, forming a superficial contusion on that area of the skin without nicking or piercing the skin, sealing that area of the skin and then collecting tissue fluid from the area of the contusion with the assistance of vacuum. The tissue fluid collected may be used for diagnostic purposes. A device for practicing the method is also disclosed.

3 Claims, 1 Drawing Sheet

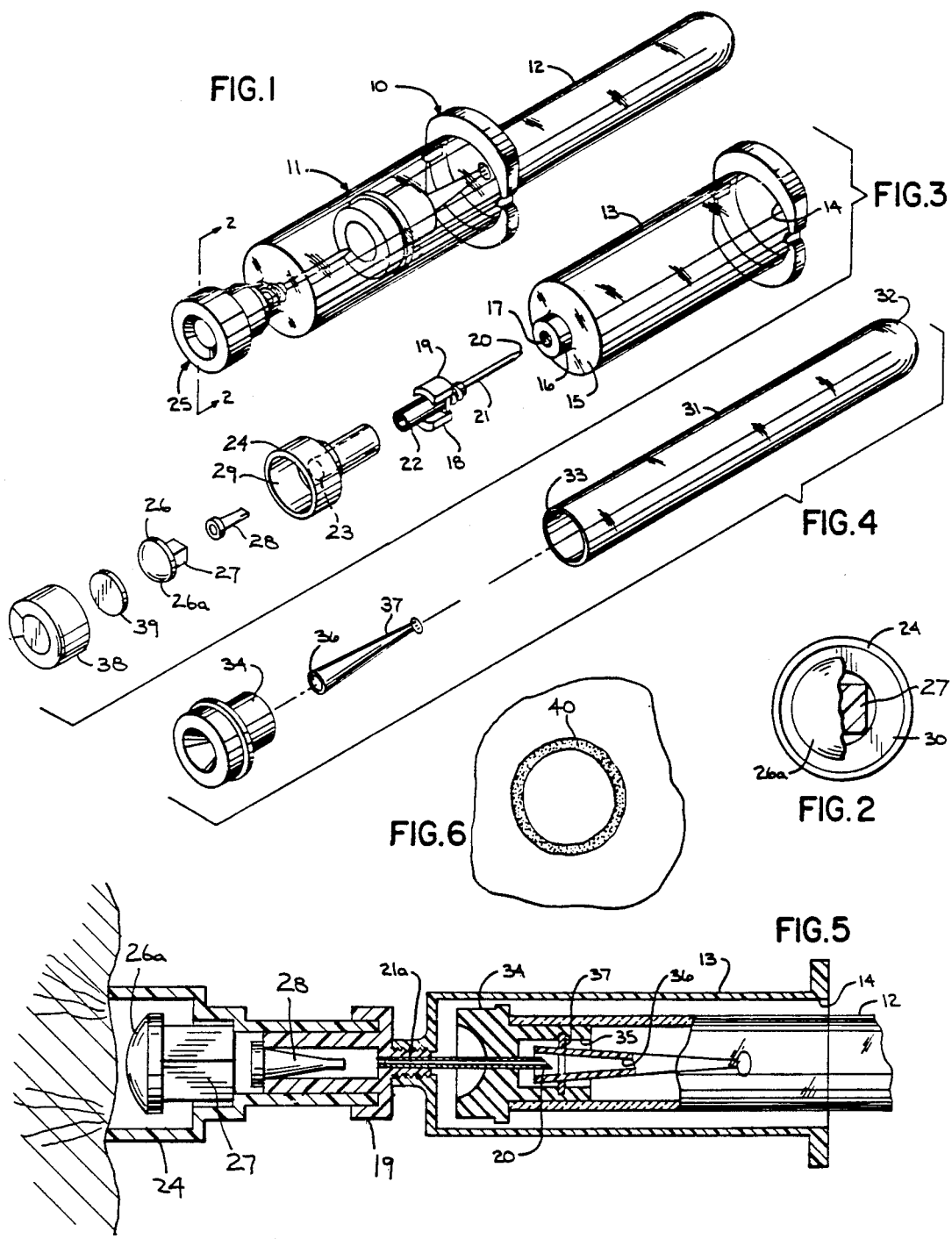

4,844,098

NON-INVASIVE COLLECTION MEANS AND METHOD

RELATED CASES

This is a continutation-in-part of my prior applications Ser. Nos. 574,901, filed Jan. 30, 1984, now abandoned, and 759,618, filed July 26, 1985, now abandoned.

TECHNICAL FIELD

The present application relates to the collection of tissue fluids. Most particularly, it relates to a method and apparatus for the non-invasive transcutaneous collection of such components from a human or animal.

BACKGROUND ART

In the past, researchers and clinicians requiring a sample of the blood of an animal usually have obtained that sample by either piercing or nicking the skin of the animal and then collecting the sample from a vein or artery. At times the sample was collected with the assistance of a vacuum.

It would obviously be advantageous to have a method of collecting fluid related to blood and blood components which does not reuqire the piercing or nicking of the skin. The nonblood intestitial and cell fluids of the skin relate to blood as determined by punch biopsies analyzed and compared by many workers.

DISCLOSURE OF THE INVENTION

The general object of the present invention are to disclose a noninvasive method for the collection of tissue fluid from a man or an animal and to disclose a device for conveniently practicing the method, not possible until now.

Briefly stated, the present invention comprises pretreating the external surface of an area of the skin (epidermis, epithelial cells) of a human or animal to clean off dead cells and increase the permeability of the skin to tissue fluids, forming a liquid coating and wetting the skin, forming a superficial contusion on that area of the skin without nicking or piercing the skin, and then, with the aid of the liquid coating and vacuum, collecting skin fluid containing the desired components from the area of the contusion. The skin fluid collected is suitable for diagnostic purposes.

The preferred device of the present invention comprises a probe having a cup-shaped member for holding a coating liquid and forming a seal with the skin at one end and means for receiving a sealed vacuum tube at the other end. The probe includes a deflector positioned within and partially filling the cup-shaped member and means for opening the seal of the vacuum tube when the cup-shaped member is sealed against the skin so that the deflector and vacuum cooperate to form a contusion and the vacuum and a coating of liquid on the skin cooperate to transfer skin fluid fluid into the vacuum tube.

In the drawings;

FIG. 1 is a perspective view of a preferred embodiment of the device for use in the method of the present invention;

FIG. 2 is an end view taken along lines 2—2 in FIG. 1;

FIG. 3 is an exploded view showing the parts of the probe of the device of FIG. 1 prior to assembly;

FIG. 4 is an exploded view showing the parts of the collection tube of the device of FIG. 1;

FIG. 5 is a schematic view showing the device applied to the skin in the practice of the method of the present invention; and FIG. 6 is an illustration showing the contusion formed upon the skin.

In FIG. 1 to 4 of the drawings, there is shown a preferred embodiment of a device which can be used in the practice of the method of the present invention. The device 10 as seen in FIG. 1 consists of a probe 11 and a collection tube 12.

Referring to FIGS. 1 to 5, it can be seen that the probe 11 includes a hollow-cylindrical housing 13 which is open at one end 14 to receive the collection tube 12. The other end 15 of the housing is closed except for a tubular central inlet 16. As seen only in FIG. 5 the inside of the inlet 16 is threaded as at 17 to receive a needle assembly 18 having a hub 19. When the needle assembly 18 is secured in the inlet 16 as seen in FIG. 1 a sharp piercing end 20 of a needle 21 projects into the housing 13. A tubular projection 22 extends outwardly from the other end of the hub 19. of the needle assembly. As seen best in FIG. 5 the hub 19 fits wihtin a central bore 23 of a cup-shaped member 24, preferably of resilient plastic, wich is part of the tip 25 of the probe 11. As seen only in FIG. 3, the tip 25 also includes a solid mushroom-shaped deflector 26, preferably of rigid plastic, which has as stem 27 adapted to fit loosely into the other end of the bore 23 of the cup-shaped member 24 and a duck-billed valve 28 for keeping liquid properly positioned in the front end of cup 24 until vacuum is applied. A septum 39 and cap 38 can be used to contain the liquid until use.

As seen best in FIG. 2, when the deflector 26 is properly positioned in the cup-shpaed member 24 an opening 30 exists between the outsdie of the head 26a of deflector 26 and the inside of the recess 29 of the cup-shaped member 24.

Turning to FIGS. 4 and 5, it can be seen that the collection tube 12 includes a glass or plastic tube 31 which is closed at one end 32 and open at the other end 33. In the completely assembled collection tube 12, as seen in FIG. 1, the open end 33 is closed by a solid resealable stopper 34. The inner end of the stopper 34 has a central recess 35 seen only in FIG. 5 in which a small fluid collection trap 37 for the skin fluid is locked in place by friction. The interior of the assembled tube 12 including the trap 37 is at a reduced pressure or vacuum. The trap 37 can be made of a gas permeable plastic or have a vent hole or notch 36 to insure that its interior is also at a reduced pressure (e.g., 100–400 mm Hg.).

As seen in FIGS. 1 and 5 the cylindrical housing 13 is sized to serve as holder for the vacuum tube 12. In FIG. 1, the tube 12 is shown sealed and in FIG. 5 the tube 12 is shown advanced within the holder 13 with the needle assembly 18 piercing the stopper 34 of the tube 12. Prior to preloading the cup-shaped member 24 with coating liquid the tube 12 can be partially advanced so that the needle point 20 is closed by but has not completely pierced the resealable stopper 34. The mouth of the cup 24 can be sealed with the septum 39 and the tearable aluminum cap 38.

In the preferred practice of the method of the present invention an area of the skin of the donor is first pretreated for one minute with a solution to clean off dead cells and to extract lipid materials from the surface. The cup 24 in the probe tip 25 of the device 10 is preloaded with a coating liquid then quickly pressed against the pretreated skin as seen in FIG. 5. The liquid in the cup 24 in the probe tip 25 forms a liquid coating on the skin which increases skin permeability and assits the transfer of the skin fluid to the vacuum tube. Keeping the outer portion of the cup-shaped member 24 in contact with the skin the collection tube 12 is then advanced within housing 13 until the point 20 of the needle 21 penetrates the resealable stopper 34. Because of cooperation of the deflector 26 and the reduced pressure in the collection tube 12 a contusion 40 is formed similar to that illustrated in FIG. 6 and the liquid on the skin, including any tissue fluid extracted from the area of the contusion within the boundary of the recess 29, is sucked through the opening 30 and transported via the needle assembly 18 into the collection trap 37.

Although a specific device for forming the contusion and collecting the desired components has been illustrated and described, it will be apparent to those skilled in the art that other types of devices which form a contusion and/or provide vacuum assistance can be used in the collection of skin fluid in accord with the teaching of the present invention. Devices that have been constructed and successfully tested include those in which the probe tip is comprised of cups of elastic rubber or rigid plastic which are nipple-like or cone-shaped and those in which the probe tip includes in place of the mushroom-shaped deflector, a member which is star-shaped, or formed of concentric rings or beads.

The preferred collection tube 12 is an evacuated tube and it is surprising that the evacuated tube can both cause a contusion and extract measurable amounts of tissue fluids. The vacuum, if desired, also could be supplied by a vacuum pump (mechanical, electric, aspirator) hydraulic fluid movement, a syringe, chemical vacuum or even mouth suction. The components possibly could also be collected from the area of the contusion without vacuum assistance, if desired. It does appear, however, that the collection of skin tissue fluid is enhanced and made reproducible by reducing the atmospheric pressure on the skin within the area of the probe tip with the liquid in contact with the skin. This is not possible with any other patented device.

Devices could also be employed in which the needle assemlby is simple a channel or tube with a piercing tip and which includes a control valve or clamp. In addition, the collection trap could be a series of connected tubes joined by a constriction, a port leading to a diagnostic device, or simply a piece of sponge-like material which could be used as such in a diagnostic test or from which the collected tissue components could be recovered.

Although the use of a single pretreatment solution has been described, additional pretreatment solutions could be used. They might be applied by spraying or in a gel-like binder, or with a bandage-like applicator.

In the preferred practice of the method of the present invention, the skin is first washed with a solution and then treated with a coating liquid comprised of tri-chlorotri-fluoroethane (Freon TF; Du Pont).

The Freon TF washing solution, which removes dead cells and contaminants, is composed of a liquid active agent to permeate the skin. The solution could also be used as a coating liquid and may contain other solvents such as polyvinyl acetate, acetone and dimethylsulfoxide (DMSO) to change the permeability of skin membranes, an analgesic and a gel or cream of high viscosity to help the probe tip form a seal with the skin. Another vehicle solution which could be used in the cup 24 might also contain anticoagulants, hormones and buffering with carrier molecules to avoid nonspecific losses due to binding or deterioration and to promote preservation, and disinfection.

The preferred solution contains the following ingredients:

| Generic Name Active Component | Preferred Concentration | Concentration Range. Active |
|---|---|---|
| COMPONENTS OF THE WASHING SOLUTION | | |
| (a) FREON TF (Trichloro-trifluoro-ethane) | 100% | 100% |
| COMPONENTS OF THE VEHICLE SOLUTION | | |
| (b) Tetrahydrozo-line hydro chloride | .025% w/v | 0.02–.05% |
| (c) Alkylaryl Polyether Alcohol | 3.0% v/v | 0.05–5.0% |
| (d) Heparin-Ammonium | 50 IU/cc | 5–100 IU/cc |
| (e) Phosphate Buffered Saline Solution (PBS) | .05 M Buffer (pH 7.2) .45 M NaCl | pH 4–8 0.2–.9 M NaCl |

In addition to tetrahydrozoline HCl (0.05%) other vaso-constricting or vasodilating compounds may be used, such as phenylephrine hydrochloride. Vasodilators are preferred.

In addition to the surface active agent used other surface active agents providing the same function and not having any detrimental effects can also be used. Representative of such surface active agents are the following: Guanidinium chloride, mercaptoethanol or other nonionic or ionic detergents.

The preferred anticoagulant solution contains ammonium heparin. However, other anticoagulants which may be used include the following: ethylenediaminetet-raacetic acid (EDTA) (0.02%), sodium heparin, sodium citrate, streptokinase or streptodornase.

Other cleansing agents than FREON TF may be used such as methyl salicylate 15.0% in methanol 70% v/v, ethanol, paraben, methylparaben, providone iodine, phenol (0.5%) antibiotics, dimethyl sulfoxide, acetone, isopropyl alcohol, chloroform, polyvinylacetate, polyvinyl alcohol, mineral oil, propylene glycol, or polyethylene glycol. In addtition an antibubble agent may be added. If desired, a pain depressing agent such as benzocaine or triethanolamine salicylate or a heat stimulating agent like methylsalicylate also may be included along with volatile solvents such as ether. Still further the addition of mild enzyme solutions such as trypsin may be useful, depending on the component(s) desired in the sample obtained.

The preferred method of collecting skin tissue fluid components comprises:

(a) Applying FREON TF solvent (1–2 drops) to a portion of hairless skin such as the forearm for 10 seconds, wiping with a clean tissue.

(b) Applying 375 microliters ($\mu$l) of a hypotonic buffered solution containing phosphate buffer 0.05 M, pH 7.2—about 30 seconds.

(c) Pressing the prode tip 25 (cup 24 preloaded with the solution used in b for forming a liquid coating), firmly to the treated skin.

(d) Forming a seal and contusion by activating the vacuum by moving the tube 12 within the housing 13 until the needle 21 pierces the stopper 34 of the vacuum tube while maintaining contact with the skin for 0.5 minutes.

(e) Stopping the action by pulling the probe tip away to break the vacuum. The skin sample is thus collected in the trap.

(f) Wiping the skin area with alcohol or a suitable antiseptic.

The preferred method results in the skin being visibly affected. It is reddened and a small "hickey" or contusion is formed. It appears that only microcapillaries are broken allowing the contusion to quickly heal and greatly reducing the risk of infection (skin punch biopsies were taken and evaluated by a certified clinical pathologist as noninvasive). A small sample, 300 $\mu l$, of sample is trapped in the collection tube. The skin is obviously still intact. There is no bleeding evident, no scab formation takes place, no clotting evidence appears, no visible scratches, nicks or piercing of the skin occurs and no infections result. There is no pain, only the reddened area or contusion which usually disappears within 10 minutes to 2 days.

The skin fluid contains many interesting chemical components some of which are given in the following chart:

SOME COMPONENTS OF THE SAMPLE

Data obtained by sending the "skin" samples to commerical clinical testing laboratories and to analytical testing labs. The skin tissue fluids thus collected were diluted 2000–3000x by the method used.

|  | Test #1a | Test #1b | Test #2 | Normal Range |
|---|---|---|---|---|
| Glucose | .05 | .08 | .05 | 70–110 mg/dl |
| BUN | 2 | .8 | 8 | 8–30 mg/dl |
| Calcium | .1 | .8 | 3.6 | 8.5–10.8 mEq/L |
| Iron | 9 | NT | 23 | 40–150 $\mu g$/dl |
| Potassium | .9 | 1.2 | 1.9 | 3.5–5 mEq/L |
| SGOT | 4 | 4 | 9 | 7–27 IU/L |
| SGPT | 10 | 1.7 | 12 | 8–30 IU/L |
| Sodium | 4 | 18 | 14 | 135–145 mEq/L |

Test #1a and Test #1b are the same sample tested at two different Labs.

Test #2 is a sample which has been concentrated about 10x, and tested at the same lab as Test #1a. This sample was lyophilized and the nonstable enzymes and gases may be lost. The sample was also analyzed for proteinaceous components and carbohydrates by colorimetric methods and specific drugs and chemicals by commercial or other assays, such as high performance liquid chromatography (HPLC).

In addition to the specific device shown in the drawings for making the contusion, other types of devices can be used including mechanical devices to form the superficial contusion such as gentle pinching or pressing devices, with or without vacuum.

The trap 37 can be fabricated in many useful configurations. Traps have been constructed with minor changes in shapes that will perform the following functions.
1. Filtration of the specimen.
2. Column purification.
3. Mixing with a series of chemicals in steps.
4. Storage of reactants separately, yet allowing easy mixing.
5. Growing microorganisms.

Post treatment of the skin after the contusion with 70% isopropyl alcohol helps prevent any possibility of infection or irritation. In addition, post treatment of the sample aids in preparing and preserving the specimen for use in a diagnostic test. For example: the sample may be further diluted with buffers such as phosphate-saline, Tris-HCl, hepes, boric acid-soidum borate. The diluent can contain protease inhibitors (i.e., dithiothreitol, 1 mM) or other ingredients to help purify the component to be tested (i.e., Affigel-Blue, Biorad Co., to remove albumin; Protein A, from staphlococcus A, to bind up IgG; Calcium Chloride to help remove fibrin).

Losses of desired constituents by nonspecific absorption can be prevented by precoating the internal surfaces of the collection device components with silicon or proteins. Preservatives such as paraben or antibiotics also may be used. The sample can be stored frozen.

The permeability of the skin (membranes of the epidermis and dermis) for diffusion of components is variably dependent upon:
1. The balance of blood pressure and atmospheric pressure;
2. The integrity of the membrane barrier;
3. active transport;
4. relative concentration, solubility and size of components;
5. hydrophobic and ionic forces between macromolecules (i.e., presence of lipid associated materials);
6. temperature; and
7. pH (hydrogen ion concentration) and ionic strength.

The method of the present invention through use of a washing solution and vehicle liquid and vacuum can suitably adjust these variables to obtain a sample of body fluid directly through the skin without pain or discomfort.

The practice of the present invention is further illustrated by the examples which follow.

EXAMPLE I

Subject - Male, Age 45. A small (about 1 cm$^2$) area of the skin on the forearm was treated with Freon TF (10 seconds) followed by 375 $\mu l$ drops of solution phosphate buffered saline (PBS) (0.05 M Buffer pH 7.2, 0.45 M NaCl) for 10 seconds in the probe tip cup of the mechanical device shown in FIGS. 1 to 4 applied to the skin. The collection tube assembly was moved within the housing to activate the vacuum. Suction was maintained for 0.5 minutes and halted by pulling away the probe tip from the skin. Thirty-eight replicate samples were taken.

The skin was not broken; and only small superficial contusions (hickies) resulted that disappeared in 48 hours.

The samples obtained in the collection trap were removed by separating the tube and unplugging the rubber stopper. The samples were tested for glucose.

An average of 0.05 mg/dl (500 PPB) were detected by an enzymatic colorimetric assay. The average coefficient of variation was 16%.

Glucose was detected at about 0.05 mg/dl by a colormetric reaction using a specific hexokinase glucose 6-phosphate dehydrogenose assay.

Protein was determined as about 100 mg/dl by color change of the indicator 3', 3", 5', 5"- tetrachlorophenol - 3, 4, 5. 6 - tetrabromosulfopthalein.

EXAMPLE II

Subject - Female, Age 39. A small (about 1 cm$^2$) area of the skin on the forearm was treated with 375 μl of solution PBS for about 10 seconds. The cone-shaped probe tip of a device made from nonflexible plastic which was connected to a vacuum source (mechanical pump: 250 mm of Hg) was pressed against the treated skin for 60 seconds with a fluid trap in series. About 300 μl of sample was recovered. The sample was tested for blood components as follows:

Carbohydrates were detected by high performance liquid chromatography (Dionex AS6 Column; pulsed amperometric detector in 0.15 M NaOH).

Thirty-three other determinations were made using various other mechanical devices described and profiles of carbohydrates in sample solutions was determined empirically to be of the same pattern (i.e., 6 major peaks) for all persons.

EXAMPLE III

A male 43 year old was sampled for total bacteria per centimeter square (cm$^2$) of skin.

A preferred device as seen in the drawings was sterilized with 70% ethanol, preloaded with sterile saline, and applied to various skin sites, arm, leg, foot, to collect material.

A comparison of "dirty" and freshly washed skin was made by culturing the resulting samples on a rich nutrient medium. As expected, the uncleansed skin had much more detectable bacteria. Even freshly cleansed skin contained about 1000 bacteria per cm$^2$. These were nonpathogenic organisms; but the method used in conjunction with the appropriate test could be used to diagnose pathogens. Thus, glucose in samples must be assayed immediately or stored so as to preserve.

EXAMPLE IV

Six nondiabetic patients and six diabetic patients were tested using the preferred device and method of the present invention to collect specimens. A colorimetric assay for glucose was employed.

Many assays were performed for each individual. The results were compared to direct blood tests using a similar assay. The results indicated that total glucose values obtained with the device and method of the present invention paralleled the blood values obtained from direct blood tests when plotted against time before and after glucose intake. Triglycerides were also elevated after glucose intake, and were detected in the samples.

A hypotonic saline pretreatment solution was used allowing 30 seconds contact before forming the contusion for most tests. Total glucose results also could be stimulated by using other additives such as glycerol. When no liquid pretreatment was used, no glucose could be found in the specimens collected. The use of other types of devices (i.e., without a deflector which pinches off an area of skin) gave irreproducible results.

EXAMPLE V

A forty-three year old male was tested using the device and method of the present invention. The device was kept in contact with skin for extended periods of time. A variety of liquid pretreatments were used with essentially the same result. After about sixty minutes of application, a blood blister was raised on the skin and a pink (hemoglobin containing) solution was obtained.

The resulting lesions took more than one week to disappear. Use of the device for short periods of less than two minutes was always noninvasive.

EXAMPLE VI

A forty-three year old male was tested, using the method and device of the present invention and various pretreatment solutions for the collection of electrolytes (sodium and potassium). Ion specific electrodes indicated the presence of the electrolytes in the transudates collected.

In several tests the ratio of thw two ions appeared to correlate with blood levels. Dimethylsulfoxide was found to increase the yields of electrolytes five-fold over the use of aqueous pretreatment solutions. Some more aggressive (i.e., detergent containing) solutions were found to encourage proportionately higher potassium levels, indicating cell disruption. A variety of cell debris was observed in samples; therefore, tests specific for cell contents could be performed.

EXAMPLE VII

A forth-three year old male was tested, with the device of the drawings using hypotonic saline as a pretreatment solution, for amino acids and protein in transudates. In a short time of application (30 seconds) equivalent reproducible amounts were detected as compared to 5 minute applications. Since phenylalanine (PA) is one of the amino acids, it is possible that this approach could be used to detect PA elevated due to phenylketonuria (PKU). Other genetic defects or inborn errors of metabolism probably could be diagnosed using specific tests.

It will be apparent to those skilled in the art that there are many reasons why it may be preferable to use the present invention rather than pierce the skin with a lance or needle. The procedure of the present invention is non-invasive and therefore has less chance of secondary infection when components are presterlized and used in a sanitary manner. The method is painless. The extrudate may be obtained by the donor or another person in a one-hand operation, without technical expertise, and is essentially foolproof. The site of extraction is less precise than that required for phlebotomies. Therefore, a sample could be obtained more easily from infants or others with small and damaged veins or in emergency silutations. In addition, the method and device are of great potential value in the development of diagnostic tests that require plasma-like or other fluid for home health care and consumer performed diagnostics.

The embodiments of the invention in which an exclusive property or privilege is claimed are defined as follows:

1. A device for use in a non-invasive method of collecting a tissue fluid sample from a human or an animal which comprises a probe having at one end a relatively rigid member for forming a contusion on the skin of said human or animal, a cup-shaped member surrounding the relatively rigid member for forming a seal with the skin about the outside of the contusion, a sealed vacuum tube in the other end of the probe, a passage in the probe extending from the cup-shaped member to means for opening the seal of the vacuum tube and a one-way valve in said passage permitting flow from the probe tip to the vacuum tube but not in the other direction.

2. A device of claim 1 in which the one-way valve is a duckbilled valve.

3. A non-invasive method for collection of tissue fluid from an animal which comprises pretreating an external surface of a selected area of the skin of the animal to clean off dead cells, applying a probe containing a coating liquid to the selected area of the skin, retaining the liquid on the selected area with the probe, forming a superficial contusion on that area of the skin without removing the probe and without nicking or piercing the skin, and then collecting any tissue fluid and said coating liquid from the area of the contusion with vacuum assistance.

* * * * *